(12) United States Patent
Padovani et al.

(10) Patent No.: US 11,517,452 B2
(45) Date of Patent: Dec. 6, 2022

(54) SURGICAL INSTRUMENT AND METHODS OF USE THEREOF

(71) Applicant: K2M, Inc., Leesburg, VA (US)

(72) Inventors: Nick Padovani, Arlington, VA (US); Joshua David Rubin, Reston, VA (US)

(73) Assignee: K2M, Inc., Leesburg, VA (US)

( * ) Notice: Subject to any disclaimer, the term of this patent is extended or adjusted under 35 U.S.C. 154(b) by 330 days.

(21) Appl. No.: 16/775,961

(22) Filed: Jan. 29, 2020

(65) Prior Publication Data

US 2020/0237529 A1 Jul. 30, 2020

Related U.S. Application Data

(63) Continuation of application No. 15/409,629, filed on Jan. 19, 2017, now Pat. No. 10,561,504.

(60) Provisional application No. 62/280,206, filed on Jan. 19, 2016.

(51) Int. Cl.
*A61F 2/46* (2006.01)
*A61B 17/16* (2006.01)
*A61B 17/00* (2006.01)

(52) U.S. Cl.
CPC ........ *A61F 2/4657* (2013.01); *A61B 17/1604* (2013.01); *A61B 17/1671* (2013.01); *A61F 2/4611* (2013.01); *A61F 2/4684* (2013.01); *A61B 2017/00712* (2013.01); *A61F 2002/4658* (2013.01)

(58) Field of Classification Search
CPC ............ A61B 17/1604; A61B 17/1671; A61B 17/1657; A61B 17/1757; A61F 2/4611; A61F 2002/4658; A61F 2/4684
See application file for complete search history.

(56) References Cited

U.S. PATENT DOCUMENTS

| | | | | |
|---|---|---|---|---|
| 6,383,188 B2* | 5/2002 | Kuslich | ............... | A61B 17/1617 606/80 |
| 6,723,126 B1 | 4/2004 | Berry | | |
| 8,277,452 B2* | 10/2012 | Graves | ............... | A61B 17/1617 606/83 |
| 8,696,672 B2* | 4/2014 | Barnhouse | .......... | A61B 17/1671 606/85 |
| 9,161,763 B2* | 10/2015 | Assell | ................ | A61B 17/7055 |
| 2004/0215198 A1 | 10/2004 | Marnay et al. | | |
| 2006/0064100 A1* | 3/2006 | Bertagnoli | ......... | A61B 17/1671 606/79 |

(Continued)

*Primary Examiner* — Matthew J Lawson
(74) *Attorney, Agent, or Firm* — Lerner, David, Littenberg, Krumholz & Mentlik, LLP

(57) ABSTRACT

A surgical instrument includes a housing, an outer shaft, an inner shaft, a trial sizer, a rod, and a head. The outer shaft is operatively coupled with the housing such that rotation of the housing causes axial displacement of the outer shaft. The outer shaft includes a keel cutter configured to form a channel in a vertebral body. The inner shaft disposed within the outer shaft. The trial sizer is configured to be received in intervertebral space. The trial sizer includes a pair of wings transitionable between a retracted position and an extended position in which the pair of wings extends transversely outward. The head is connected to the rod, wherein the head is operatively coupled with the pair of wings such that axial displacement of the rod causes transition of the pair of wings between the retracted and extended positions.

20 Claims, 13 Drawing Sheets

(56) References Cited

U.S. PATENT DOCUMENTS

| | | |
|---|---|---|
| 2007/0078483 A1* | 4/2007 | Ewaschuk .............. A61B 17/29 |
| | | 606/205 |
| 2007/0118145 A1 | 5/2007 | Fischer et al. |
| 2008/0147193 A1 | 6/2008 | Matthis et al. |
| 2008/0269756 A1 | 10/2008 | Tomko et al. |
| 2010/0211119 A1 | 8/2010 | Refai et al. |
| 2012/0101582 A1 | 4/2012 | Raiszadeh et al. |
| 2014/0031935 A1 | 1/2014 | Donner et al. |
| 2014/0121774 A1 | 5/2014 | Glerum et al. |
| 2014/0243982 A1 | 8/2014 | Miller |
| 2015/0282797 A1 | 10/2015 | O'Neil et al. |
| 2017/0215767 A1* | 8/2017 | Ziemek ................ A61B 17/025 |

\* cited by examiner

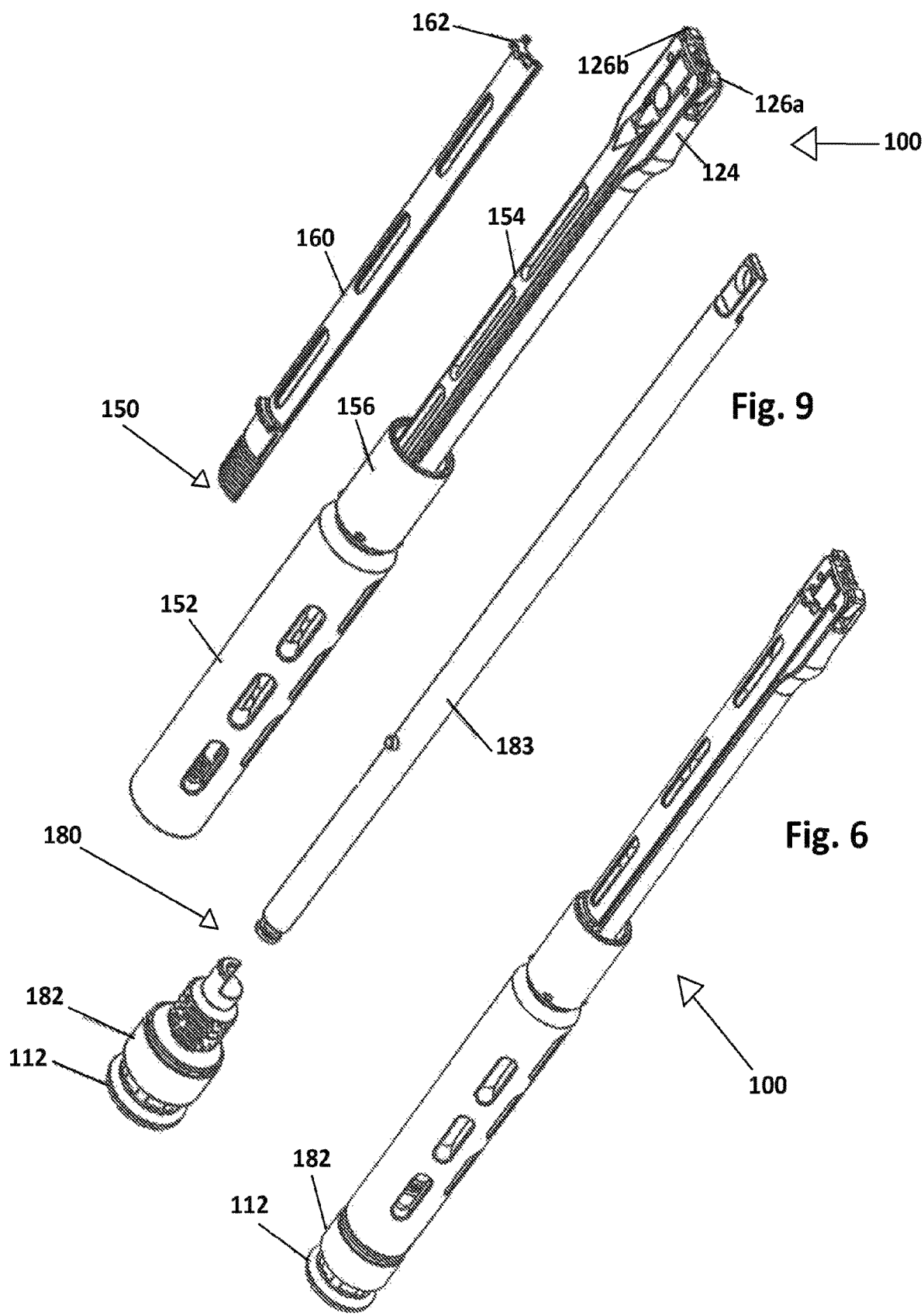

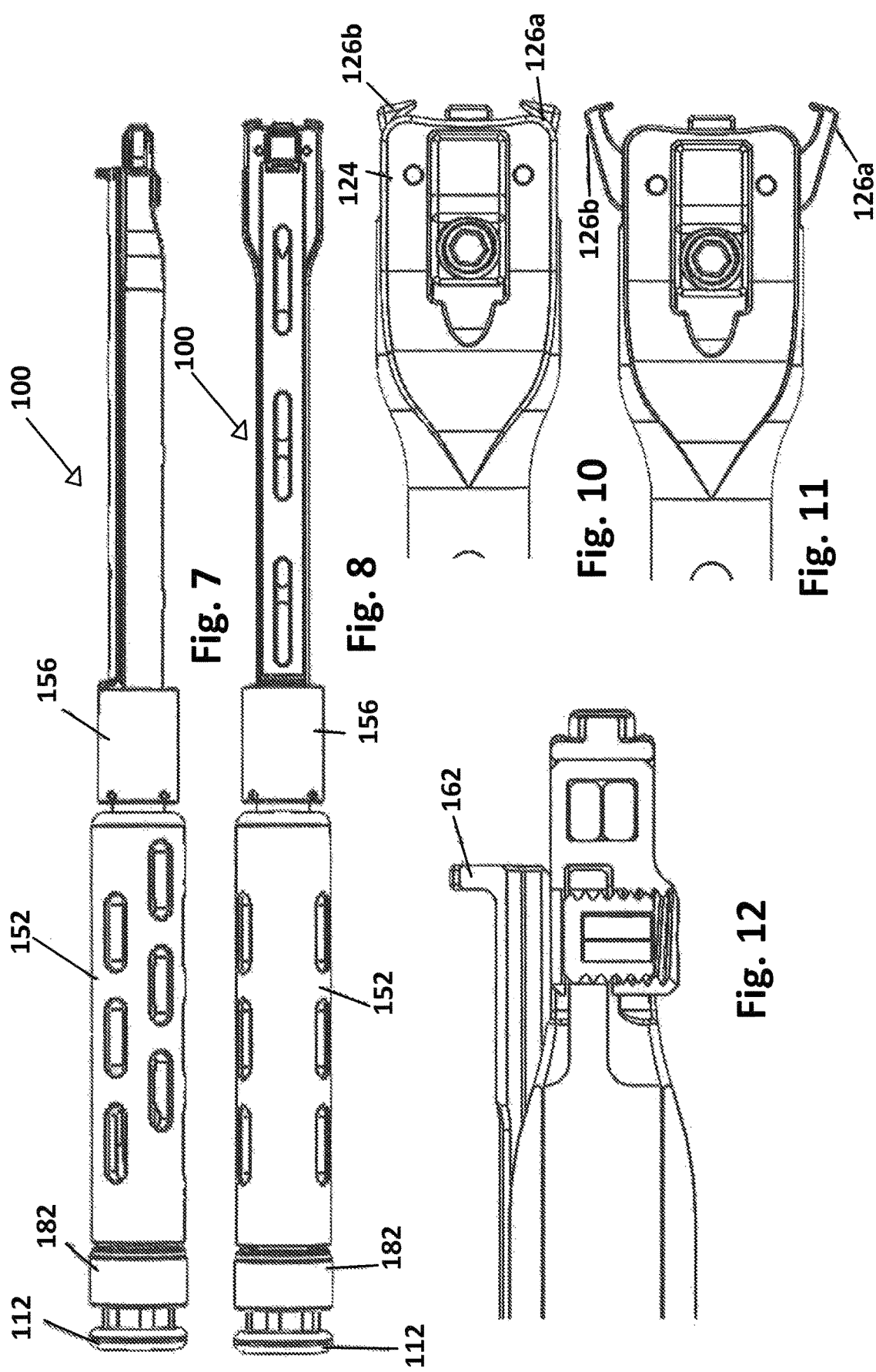

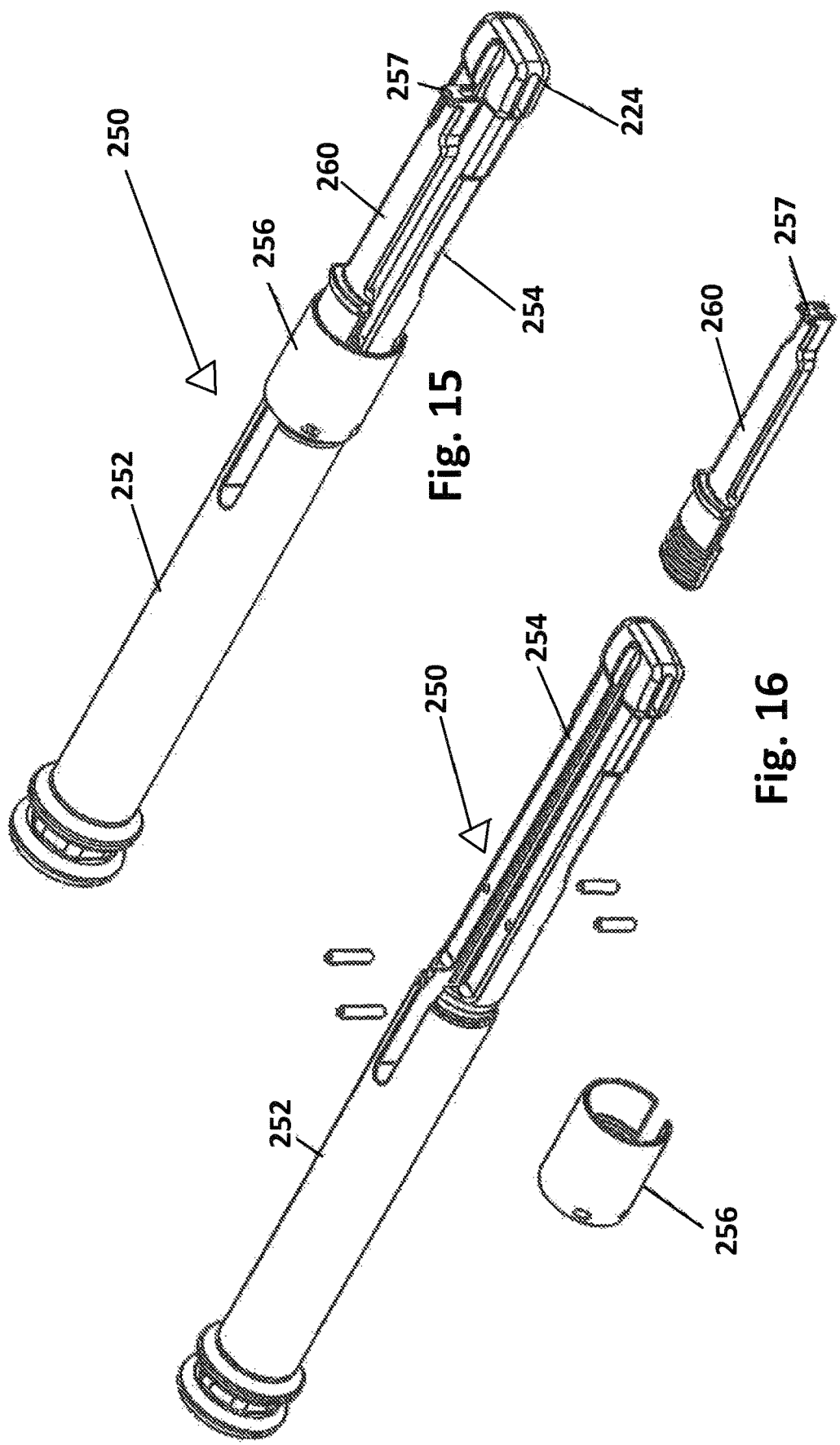

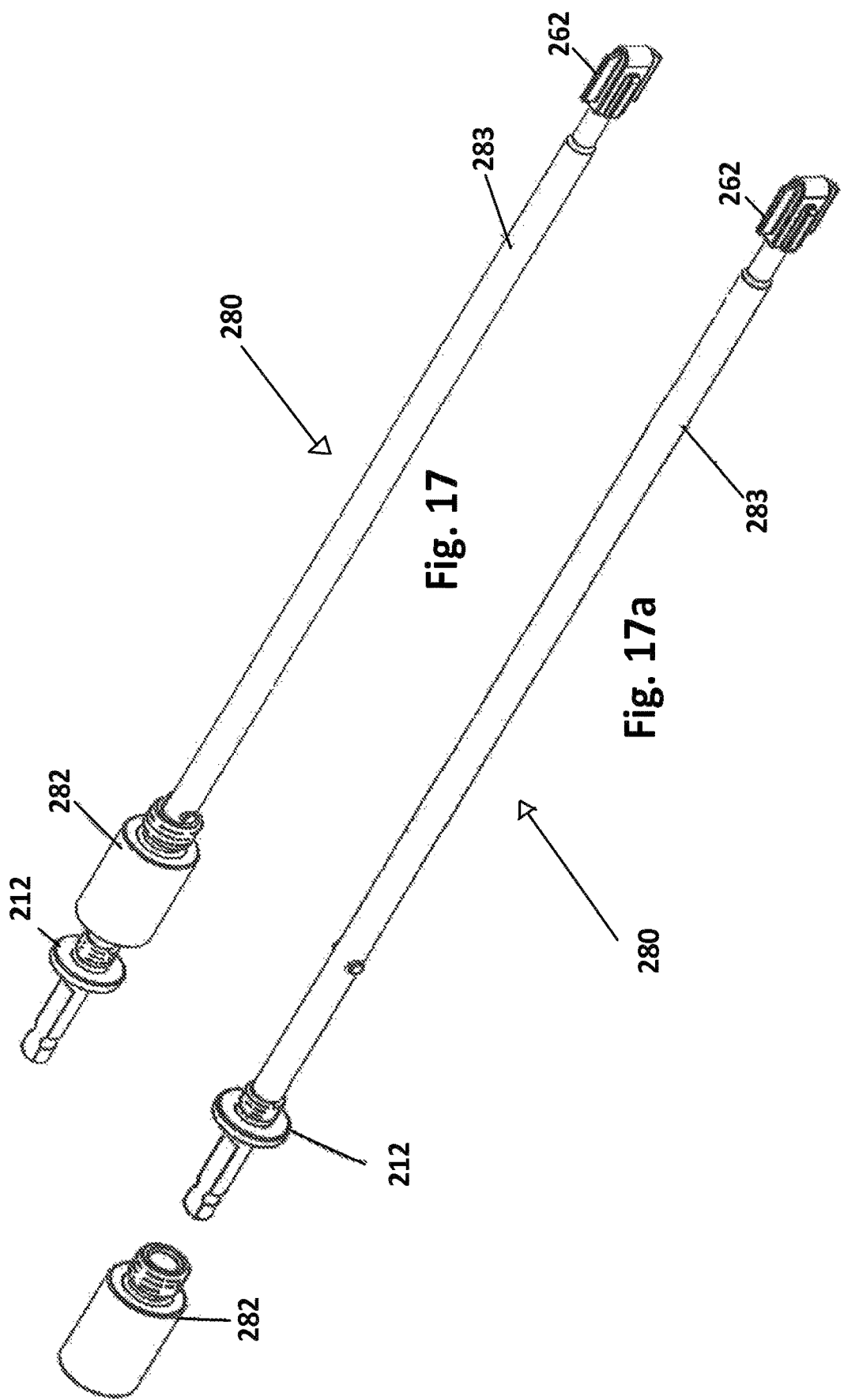

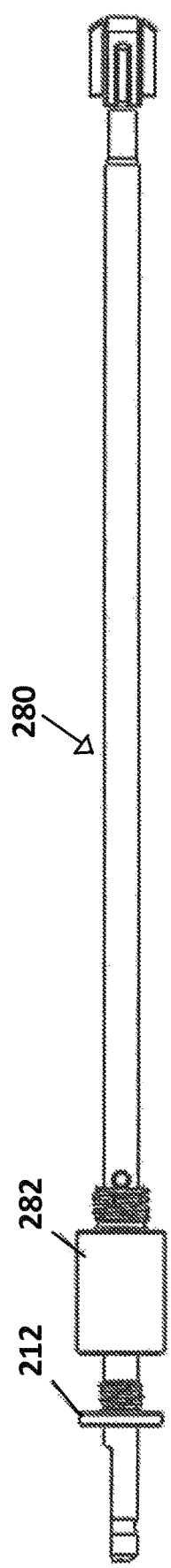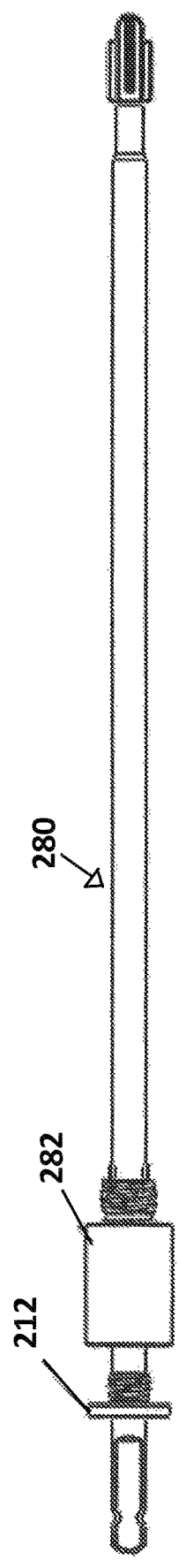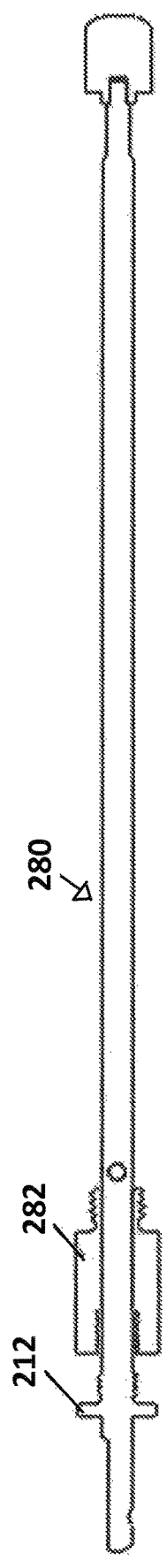

SURGICAL INSTRUMENT AND METHODS OF USE THEREOF

CROSS-REFERENCE TO RELATED APPLICATION

The present application is a continuation of U.S. patent application Ser. No. 15/409,629, filed on Jan. 19, 2017, which claims priority to, and the benefit of, U.S. Provisional Patent Application Ser. No. 62/280,206, filed on Jan. 19, 2016, the entire contents of which are incorporated by reference herein.

BACKGROUND

1. Technical Field

The present disclosure relates to an instrument for spinal surgery and, more particularly, to surgical instruments and methods for forming a keel channel in vertebral bodies.

2. Discussion of Related Art

Surgical procedures are performed to correct problems with displaced, damaged, or degenerated intervertebral discs due to trauma, disease, or aging. One of the most common procedures is spinal fusion. However, total disc replacement procedures are being utilized as an alternative to spinal fusion. The replacement procedure involves implantation of devices designed to replace the functions of the intervertebral disc and thus preserve motion that is lost through a spinal fusion.

The implant generally has an implant body and a keel structure, which can augment anti-migration features of the implant and further stabilize the position of the implant within the intervertebral space. Keel structures may extend above the upper surface and/or below the lower surface. Keel structures may be canted or generally perpendicular to the surface from which they extend. During implantation the keel structures can be inserted into keel channels formed in the adjacent vertebrae. Apertures may be provided along the length of the keel, or a portion thereof, to permit bony ingrowth through the keel structures.

Current surgical procedures utilize a trial sizer instrument and a separate keel cutter. The trial sizer may be inserted into the intervertebral space to determine the size of an appropriate implant required to achieve the desired disc height. The keel cutter is then advanced into the intervertebral space to form channels in the vertebral bodies for receiving the keel structures that are present on the implant.

Therefore, a continuing need exists for an improved device and a method for determining a desired implant size and forming a keel channel that can minimize the number of instruments, steps, and time involved in a surgical procedure.

SUMMARY

In accordance with an embodiment of the present disclosure, a surgical instrument includes a housing, an outer shaft, an inner shaft, a trial sizer, a rod, and a head. The outer shaft is operatively coupled with the housing such that rotation of the housing causes axial displacement of the outer shaft. The outer shaft includes a keel cutter configured to define a channel in a vertebral body. The inner shaft is disposed within the outer shaft. The trial sizer is configured to be received in intervertebral space. The trial sizer includes a pair of wings transitionable between a retracted position and an extended position in which the pair of wings extends transversely outward. The head is connected to the rod, wherein the head is operatively coupled with the pair of wings such that axial displacement of the rod causes transition of the pair of wings between the retracted and extended positions.

In an embodiment, the outer shaft may include a pair of keel cutters.

In another embodiment, the head may include grooves and each grooves defines an acute angle with respect to a longitudinal axis of the rod. Each of the wings may include a guide configured to be received in the respective groove of the head.

In yet another embodiment, the trial sizer may include pins and define bores dimensioned to receive the respective pins. In particular, each of the wings may define a lateral slot configured to slidably receive one of the pins.

In yet another embodiment, the keel cutter may be transitionable between an extended position and a retracted position, wherein the keel cutter extends over the trial sizer when the keel cutter is in the extended position.

In still yet another embodiment, the surgical instrument may further include a wheel operatively coupled with the rod. Rotation of the wheel may cause axial displacement of the rod.

In still yet another embodiment, the housing is rotatable about the outer shaft.

In an embodiment, the trial sizer may have a width ranging from about 14 mm to about 20 mm. Alternatively, the trial sizer may have a width ranging from about 18 mm to about 30 mm.

In still yet another embodiment, the head may be tapered.

In still yet another embodiment, the outer shaft may have a plurality of openings.

In still another embodiment, a distal-most end of the keel cutter may be tapered. The keel cutter may extend along a longitudinal axis of the outer shaft. The keel cutter may be centered between the wings.

In accordance with another aspect of the present disclosure, a method of forming a keel channel in a vertebral body is disclosed. The method includes inserting a trial sizer of a keel cutting instrument into an intervertebral space and transitioning a pair of wings of the trial sizer from a retracted position to an extended position. The pair of wings extends transversely outward in the extended position. The method also includes translating a keel cutter of the keel cutting instrument into a vertebral body to form a keel channel and removing the keel cutting instrument from the intervertebral space. The method includes placing an implant into the intervertebral space.

In an embodiment, transitioning the pair of wings of the trial sizer may include centering the trial sizer within the intervertebral space.

In another embodiment, the method may further include placing the keel cutter against a vertebral body prior to translating the keel cutter.

In yet another embodiment, translating the keel cutter may include rotating a housing of the keel cutting instrument. The housing being rotatably coupled with an outer shaft of the keel cutting instrument such that the keel cutter disposed on the outer shaft extends over the trial sizer.

In still yet another embodiment, placing the implant in the intervertebral space may include positioning a keel structure of the implant into the keel channel defined in the vertebral body.

BRIEF DESCRIPTION OF THE DRAWINGS

Various aspects of the present disclosure are described hereinbelow with reference to the drawings, wherein:

FIG. 6 is a perspective view of a keel cutter instrument in accordance with another embodiment of the present disclosure;

FIG. 7 is a side view of the keel cutter instrument of FIG. 6;

FIG. 8 is a top view of the keel cutter instrument of FIG. 8;

FIG. 9 is an exploded perspective view of the keel cutter instrument of FIG. 6 with parts separated;

FIGS. 10 and 11 are partially enlarged top views of the keel cutter instrument of FIG. 6;

FIG. 12 is a partially enlarged side view of the keel cutter instrument of FIG. 6;

FIG. 15 is a perspective view of an outer assembly of the keel cutter instrument of FIG. 13;

FIG. 16 is an exploded perspective view of the outer assembly of FIG. 15 with parts separated;

FIG. 17 is a perspective view of an inner assembly of the keel cutter instrument of FIG. 13;

FIG. 17A is an exploded perspective view of the inner assembly of FIG. 17 with parts separated;

FIG. 18 is a top cross-sectional view of the inner assembly of FIG. 17;

FIG. 19 is a side view of the inner assembly of FIG. 17;

FIG. 20 is a top view of the inner assembly of FIG. 17; and

DETAILED DESCRIPTION

Figure 1A:
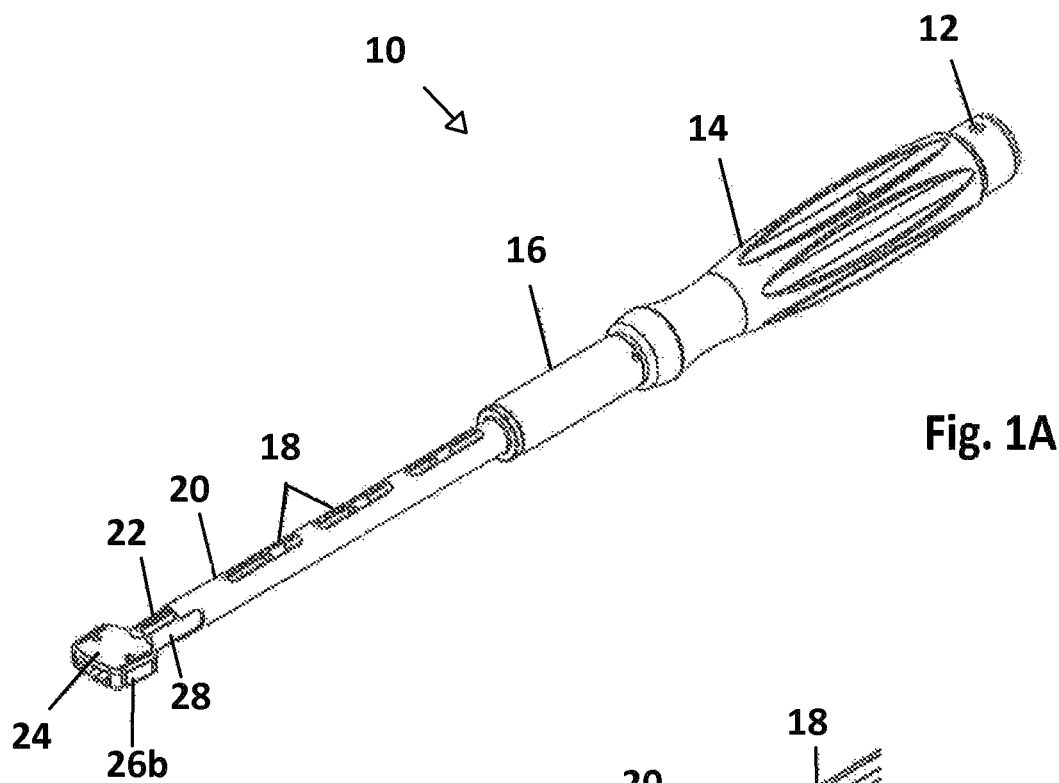
FIG. 1A is a perspective view of a keel cutter instrument in accordance with an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is farthest from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1B:
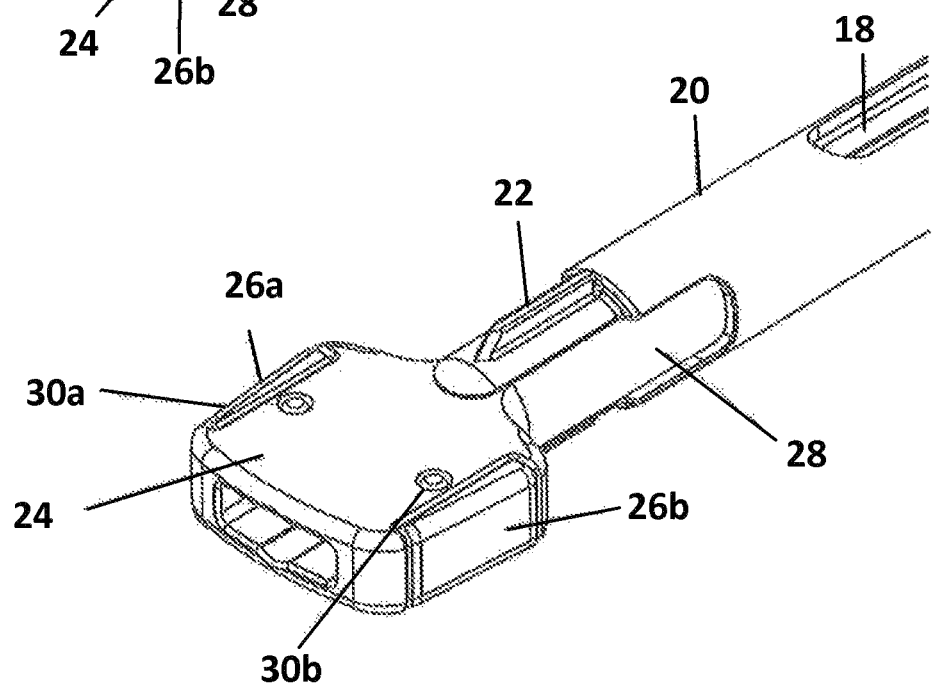
FIG. 1B is a partially enlarged perspective view of a distal portion of the keel cutter instrument of FIG. 1A.

With reference to FIGS. 1A and 1B, a keel cutter instrument in accordance with an embodiment of the present disclosure is generally shown as a keel cutter instrument 10. Keel cutter instrument 10 may be utilized to define a properly aligned keel channel or channel in a vertebral body for receiving a keel structure of an intervertebral implant. In particular, keel cutter instrument 10 enables formation of a keel channel in a vertebral body, while ensuring proper placement of keel cutter instrument 10 within an intervertebral space such that the channel may be, e.g., centered, in the vertebral body. Keel cutter instrument 10 includes an outer shaft 20, a housing 16 rotatably coupled with outer shaft 20, and a keel cutter 22 coupled with the outer shaft 20. Rotation of housing 16 causes axial displacement of keel cutter 22, as will be discussed hereinbelow. Keel cutter instrument 10 further includes an inner shaft 28 at least partially disposed within outer shaft 20 and a trial sizer 24 connected to inner shaft 28. Trial sizer 24 includes a pair of wings 26a, 26b transitionable between a retracted state (FIG. 1B) and a deployed state (FIG. 2B) to enable proper placement of trial sizer 24 in the intervertebral space, as will be described hereinbelow.

Figure 1C:
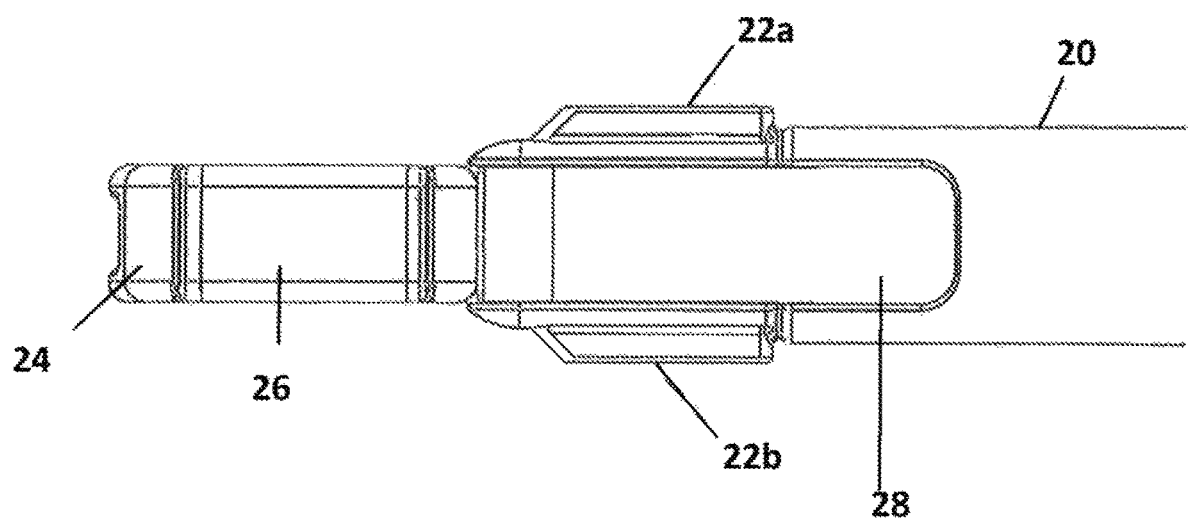
FIG. 1C is a partially enlarged side view of the distal portion of the keel cutter instrument of FIG. 1B.
Figure 1D:
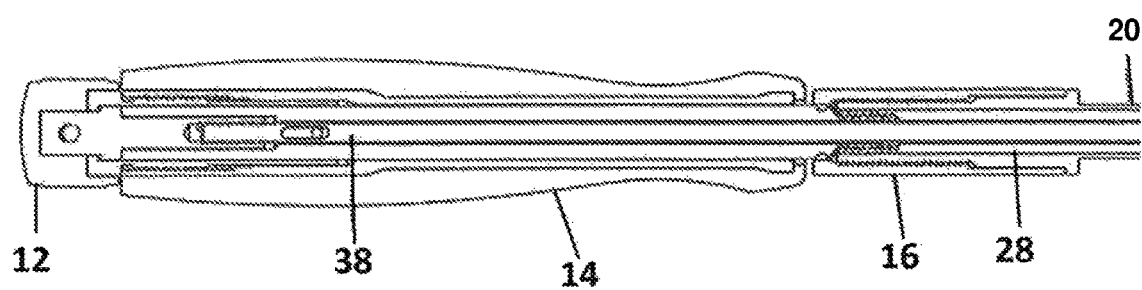
FIG. 1D is a partially enlarged cross-sectional view of a proximal portion of the keel cutter instrument of FIG. 1A.

With reference to FIGS. 1B-1D, outer shaft 20 is dimensioned to be slidably disposed on inner shaft 28. Housing 16 is threadably coupled with outer shaft 20 such that rotation of housing 16 causes axial displacement of outer shaft 20, which, in turn, causes axial displacement of keel cutters 22a, 22b. Keel cutter instrument 10 discloses a pair of keel cutters 22a, 22b disposed on opposite sides of outer shaft 20. However, it is envisioned that a single keel cutter may be utilized. Outer shaft 20 may define a plurality of openings 18 to facilitate sterilization of keel cutter instrument 10.

With continued reference to FIGS. 1B-1D, at least a portion of inner shaft 28 extends through a cover 14. Cover 14 is stationary and provides a gripping surface for the clinician. Inner shaft 28 is coupled with trial sizer 24. The shape and size of trial sizer 24 may be tailored to the particular surgical procedure being performed.

Figure 2A:
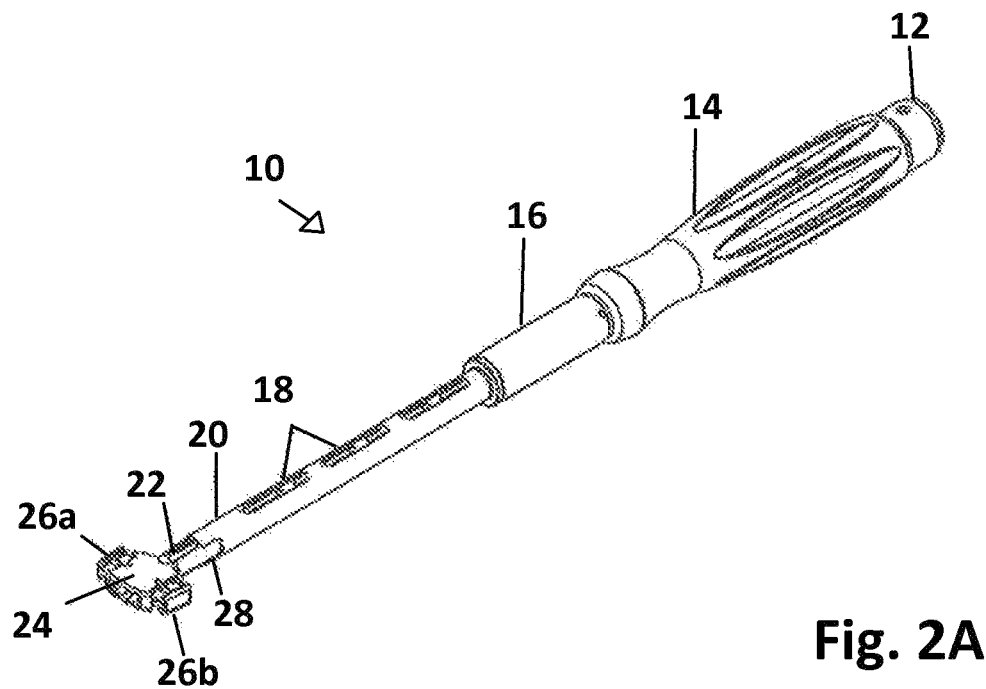
FIG. 2A is a perspective view of the keel cutter instrument of FIG. 1A illustrating a pair of wings in an extended state.
Figure 2B:
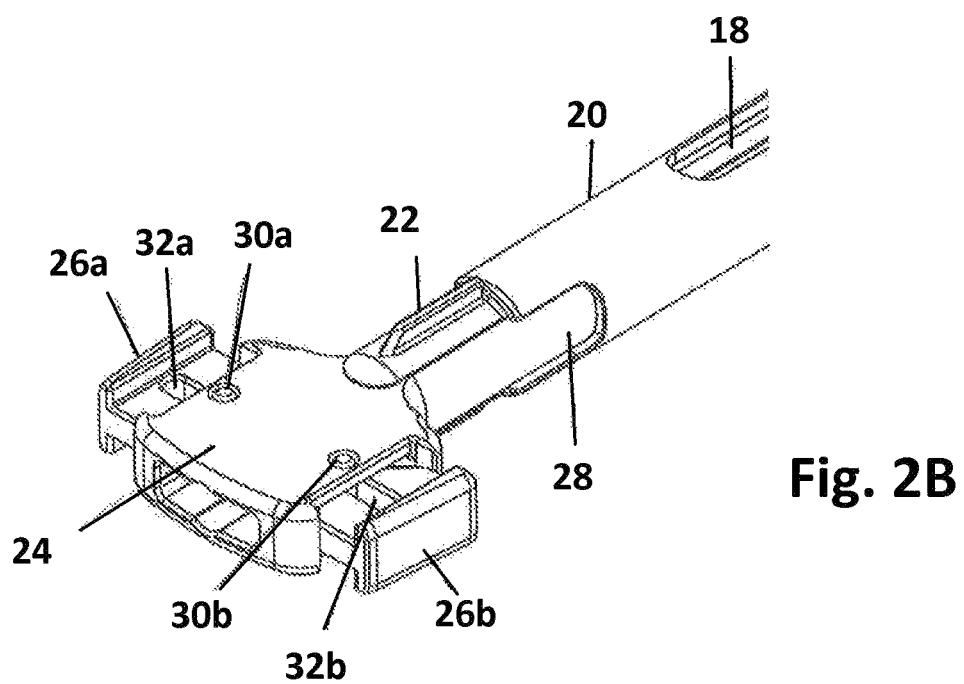
FIG. 2B is a partially enlarged perspective view of the keel cutter instrument of FIG. 2A illustrating the pair of wings in the extended state.
Figure 2C:
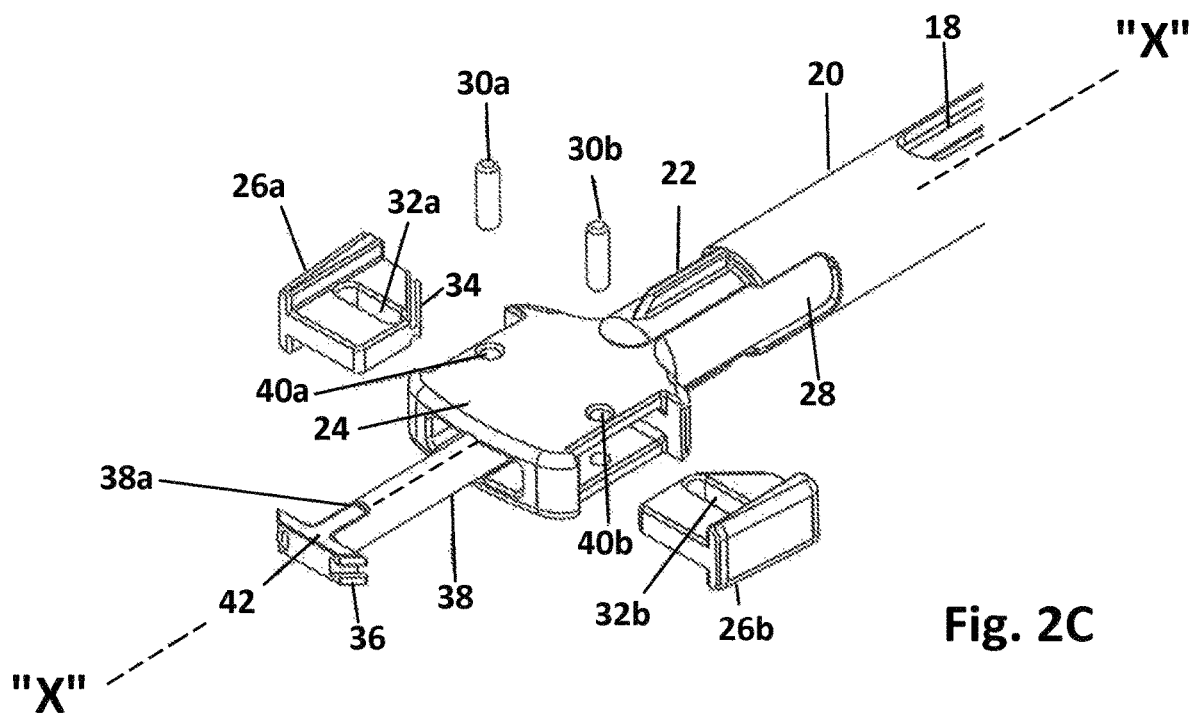
FIG. 2C is an exploded perspective view of the keel cutter instrument of FIG. 2B with parts separated.

With reference to FIGS. 2A-2C, trial sizer 24 includes wings 26a, 26b transitionable between a retracted state (FIG. 1B) and a deployed state (FIG. 2B). Keel cutter instrument 10 further includes a wheel 12 and a rod 38 (FIG. 2C). Rod 38 is rotatably coupled with wheel 12 such that rotation of wheel causes axial displacement of rod 38. Rod 38 is slidably disposed within inner shaft 28. Rod 38 operatively connects wheel 12 with head 42 disposed at a distal end 38a of rod 38. Head 42 is tapered along a longitudinal axis "X-X" defined by rod 38. Head 42 defines a pair of grooves 36 defining an acute angle with respect to longitudinal axis "X-X".

With continued reference to FIGS. 2A-2C, the pair of wings 26a, 26b may increase the width of the trial sizer 24 by, e.g., about 4 mm, when transitioned from the retracted state to the deployed state. Transitioning of the pair of wings 26a, 26b from the retracted state to the deployed state enables proper placement of trial sizer 24 within the intervertebral space. In this manner, trial sizer 24 may be properly centered in the intervertebral space. For example, the pair of wings 26a, 26b may engage the uncinated process of a cervical vertebra when the pair of wings 26a, 26b is in the deployed states to effect centering of trial sizer 24. In this manner, centering trial sizer 24 within the intervertebral space enables proper placement of the channel formed by keel cutters 22a, 22b in a vertebral body.

With particular reference to FIG. 2C, trial sizer 24 defines holes 40a, 40b dimensioned to receive respective pins 30a, 30b. Each wing 26a, 26b defines a respective transverse slot 32a, 32b configured to receive respective pin 30a, 30b. In addition, each wing 26a, 26b includes a projection 34 defining an acute angle with respect to longitudinal axis "X-X." Projections 34 are configured to be slidably received in respective grooves 36 defined in head 42. Axial displacement of rod 38 causes transition of the pair of wings 26a, 26b between the retracted and deployed states. Accordingly, rotation of wheel 12 in a first direction causes axial displacement of rod 38 in a distal direction. Such movement causes projections 34 on the pair of wings 26a, 26b to slide within respective grooves 36 defined in head 42 such that the pair of wings 26a, 26b transitions to the deployed state (FIGS. 2A and 2B). When the user rotates wheel 12 in a second direction opposite of the first direction, the pair of wings 26a, 26b transitions to the retracted position (FIGS. 1A and 1B).

Figure 3A:
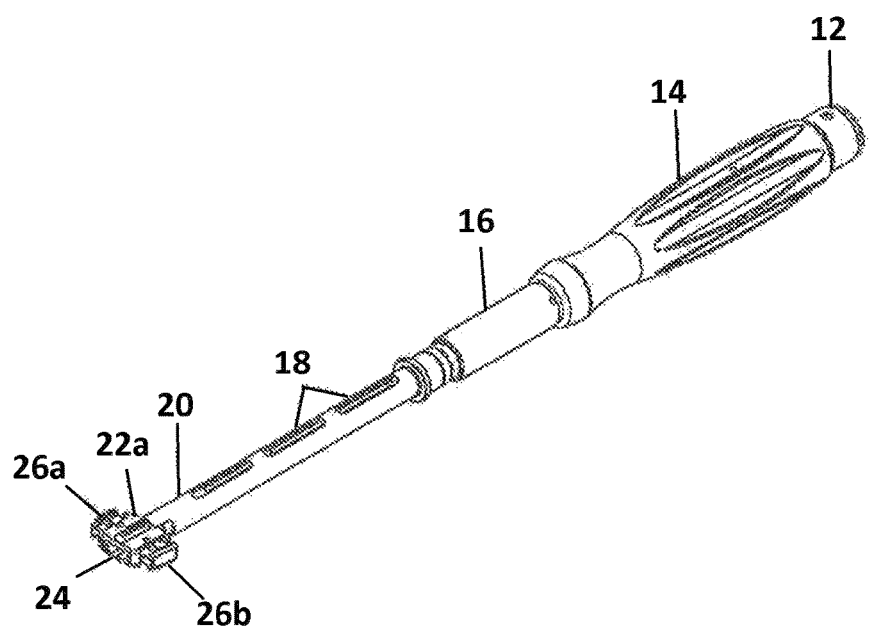
FIG. 3A is a perspective view of the keel cutter instrument of FIG. 1A.
Figure 3B:
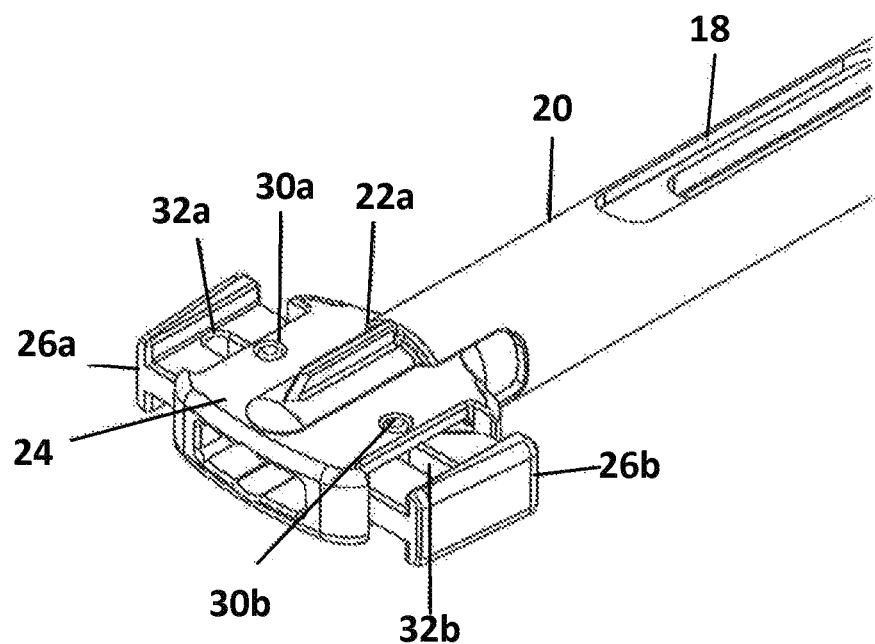
FIG. 3B is a partially enlarged perspective view of the keel cutter instrument of FIG. 3A illustrating the keel cutter in the extended state.
Figure 3C:
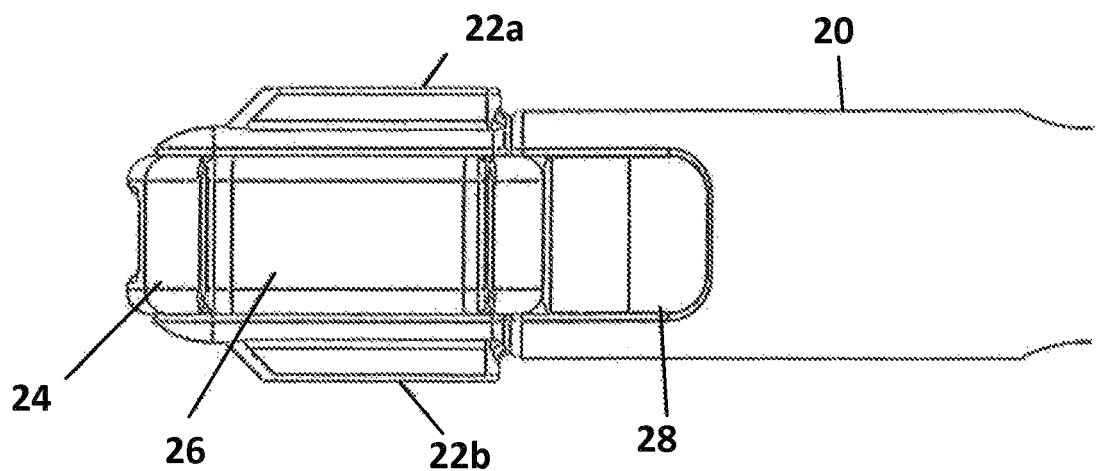
FIG. 3C is a partially enlarged side view of the keel cutter instrument of FIG. 3B.

With reference now to FIGS. 3A-3C, keel cutters 22a, 22b extend along longitudinal axis "X-X" (FIG. 2C). Keel cutters 22a, 22b may be tapered to facilitate insertion into bone. Keel cutters 22a, 22b may be centered with respect to trial sizer 24. Keel cutters 22a, 22b may be moved distally to define keel channels in a vertebral body. Specifically, the clinician may rotate housing 16 in a first direction, which, in turn, causes axial displacement of outer shaft 20 in a distal direction. In this manner, each of keel cutters 22a, 22b forms a channel in a vertebral body while keel cutters 22a, 22b extend over trial sizer 24 (FIGS. 3B and 3C). However, when the clinician rotates housing 16 in a second direction opposite of the first direction, keel cutters 22a, 22b move proximally (FIG. 1B). Combining a keel cutter instrument with a trial sizer instrument simplifies the procedure by allowing the clinician to determine the size of the implant and simultaneously prepare the disc space for inserting the implant, while ensuring proper placement of the trial sizer within the intervertebral space such that proper, e.g., centered, formation of a keel channel in a vertebral body is effected.

Figure 4A:
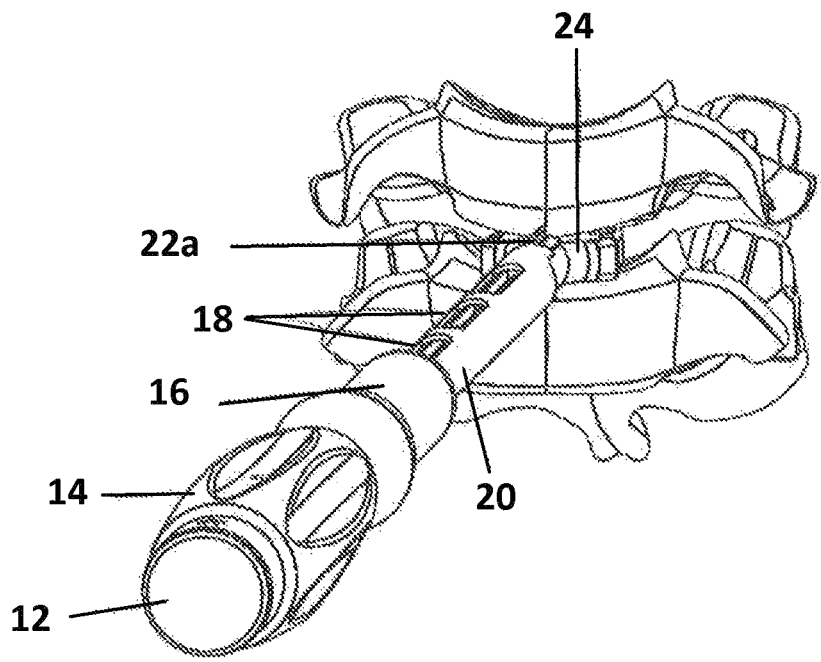
FIGS. 4A-5C are perspective views of the keel cutter instrument of FIG. 1A illustrating use thereof.
Figure 4B:
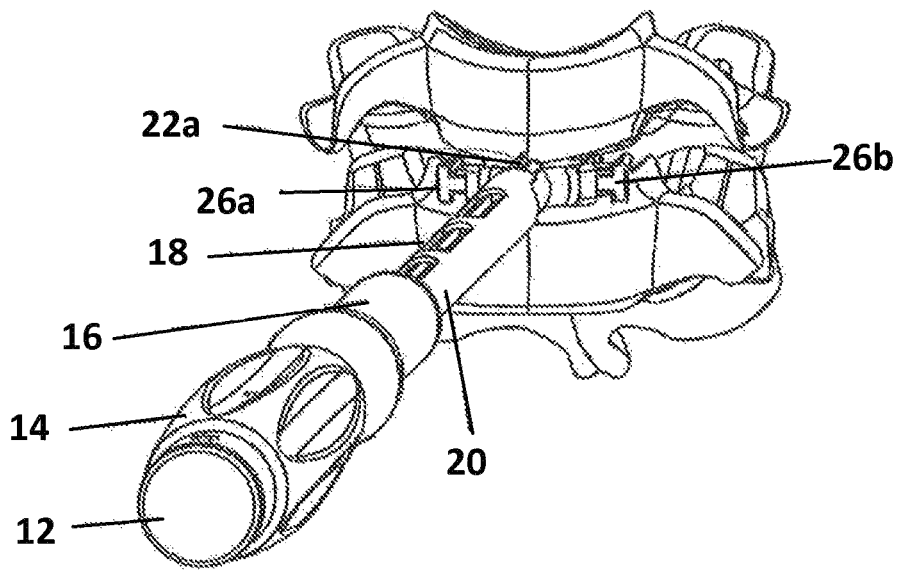
Figure 5A:
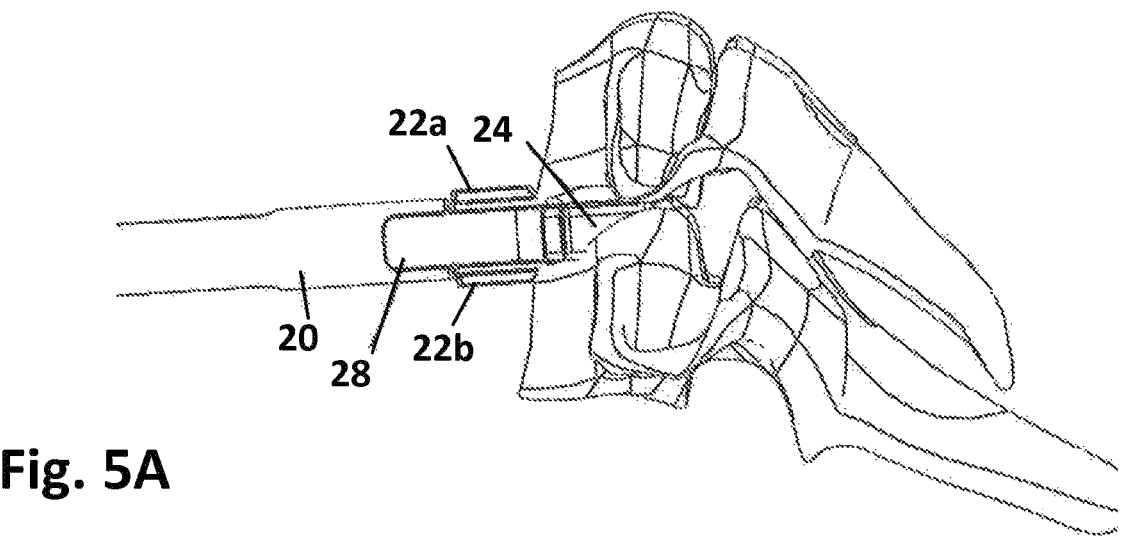
Figure 5B:
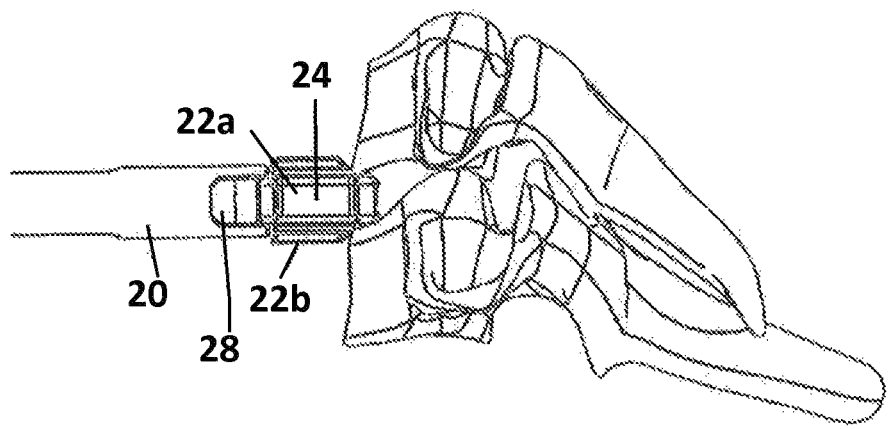
Figure 5C:
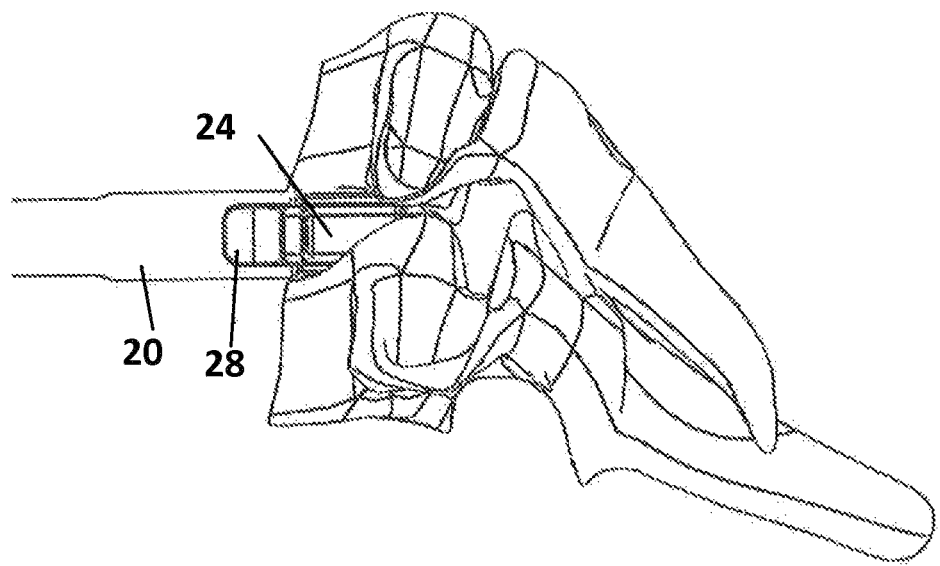
Figure 21:
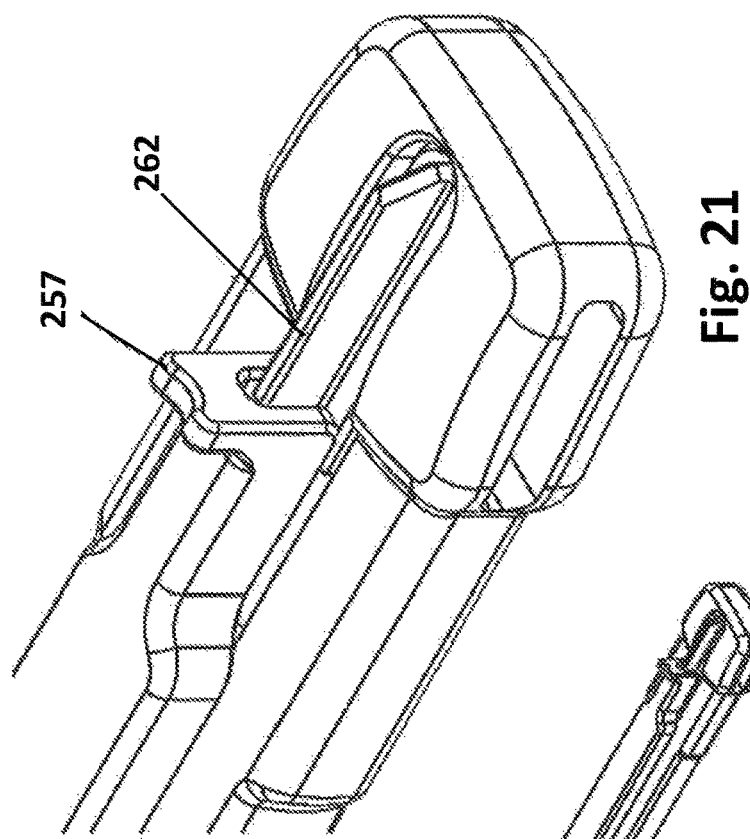
FIG. 21 is a partially enlarged perspective view of the keel cutter instrument of FIG. 13.

With reference to FIGS. 4A-5C, in use, the clinician initially prepares the intervertebral space. Trial sizer 24 is inserted into the prepared intervertebral space (FIG. 4A). At this time, wheel 12 is rotated to transition the pair of wings 26a, 26b to the deployed state (FIG. 4B). In this manner, trial sizer 24 may be properly centered within the intervertebral space. At this time, keel cutters 22a, 22b may be flush against or abut a vertebral body. The clinician may rotate housing 16, which, in turn, moves keel cutters 22a, 22b distally over trial sizer 24 (FIG. 5B), thereby forming the desired keel channels in the vertebral bodies (FIG. 5C). Optionally, wheel 12 can be rotated in an opposite direction so that the pair of wings 26a, 26b can be transitioned to the retracted state. Upon formation of the channels, keel cutter instrument 10 may be removed from the surgical site. Thereafter an implant (not shown) may be inserted into the intervertebral space such that a keel structure of the implant is received in at least one of the keel channels formed by keel cutters 22a, 22b.

Trial sizer 24 in the retracted state may have a width ranging from about 14 mm to about 20 mm. For example, trial sizer 24 may have a width of about 16 mm. Trial sizer 24 may have a width of about 18 mm when used for cervical implants. The width may range from about 18 mm to about 30 mm such as, e.g., 22 mm. For example, the width may be about 26 mm when used for lumbar implants.

It is contemplated that a keel cutter instrument kit for use with cervical implants may include a plurality of keel cutter instruments 10 having different dimensions. For example, the kit may include a first keel cutter instrument 10 including a trial sizer 24 having a width of about 14 mm, a second keel cutter instrument 10 having a trial sizer 24 having a width of about 16 mm, a third keel cutter instrument 10 having a trial sizer 24 with a width of about 18 mm, and a fourth keel cutter instrument 10 having a trial sizer 24 with a width of about 20 mm.

It is further contemplated that a keel cutter instrument kit for use with lumbar implants may include a first keel cutter instrument 10 including a trial sizer 24 having a width of about 18 mm, a second keel cutter instrument 10 having a trial sizer 24 having a width of about 22 mm, a third keel cutter instrument 10 having a trial sizer 26 with a width of about 18 mm, and a fourth keel cutter instrument 10 having a trial sizer 24 with a width of about 30 mm.

With reference now to FIGS. 6 and 9, there is provided a keel cutter instrument 100 in accordance with another embodiment of the present disclosure. Keel cutter instrument 100 includes an outer assembly 150 and an inner assembly 180. Outer assembly 150 includes a handle 152, an elongate member 154 extending from handle 152, a rotatable sleeve 156, and an outer member 160 having a keel cutter 162. Outer member 160 is operatively coupled with rotatable sleeve 156 such that rotation of rotatable sleeve 156 causes axial displacement of outer member 160. Elongate member 154 includes a trial sizer 124 including a pair of wings 126a, 126b transitionable between a retracted position and a deployed position to provide proper placement of trial sizer 124 within an intervertebral space, as described hereinabove with respect to keel cutter instrument 10.

Inner assembly 180 includes an inner member 183 operatively coupled with the pair of wings 126a, 126b such that axial displacement of inner member 183 transitions the pair of wings 126a, 126b between the retracted and deployed positions. Inner member 183 is slidably received through elongate member 152. In addition, inner assembly 180 further includes a coupling member 182 threadably coupled with handle 152. A wheel 112 is rotatably coupled with coupling member 182 and inner member 183 such that rotation of wheel 112 causes axial displacement of inner member 183, which, in turn, causes transition of the pair of wings 126a, 126b between the retracted and deployed positions.

With reference now to FIGS. 7 and 8, coupling member 182 may be selectively engaged with handle 152 to determine an angular orientation of the pair of wings 126a, 126b when in the deployed position. For example, by shortening the distance between wheel 112 and handle 152 through rotation of coupling member 182, the pair of wings 126a, 126b may provide a greater angle between the pair of wings 126a, 126b when in the deployed position. When wheel 112 is rotated, the pair of wings 126a, 126b transition between the retracted and deployed positions. The method of use of keel cutter instrument 100 is substantially identical to the method described hereinabove with respect to keel cutter instrument 10, and thus will not be described herein.

Figure 13:
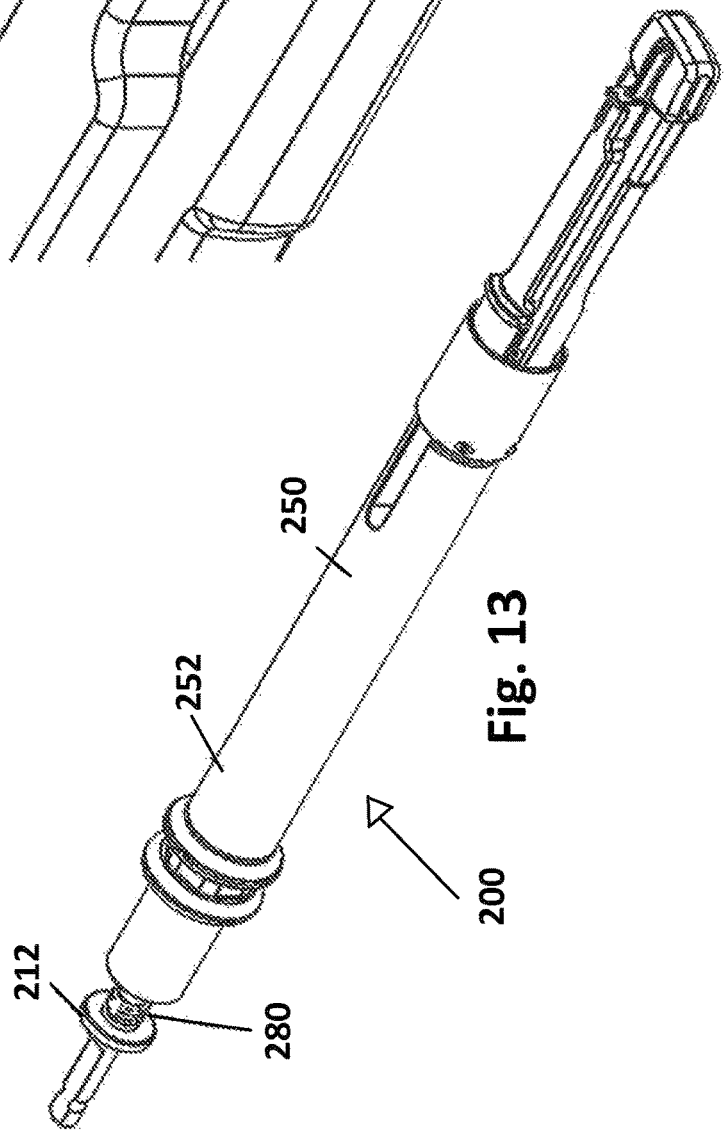
FIG. 13 is a perspective view of a keel cutter instrument in accordance with another embodiment of the present disclosure.
Figure 14:
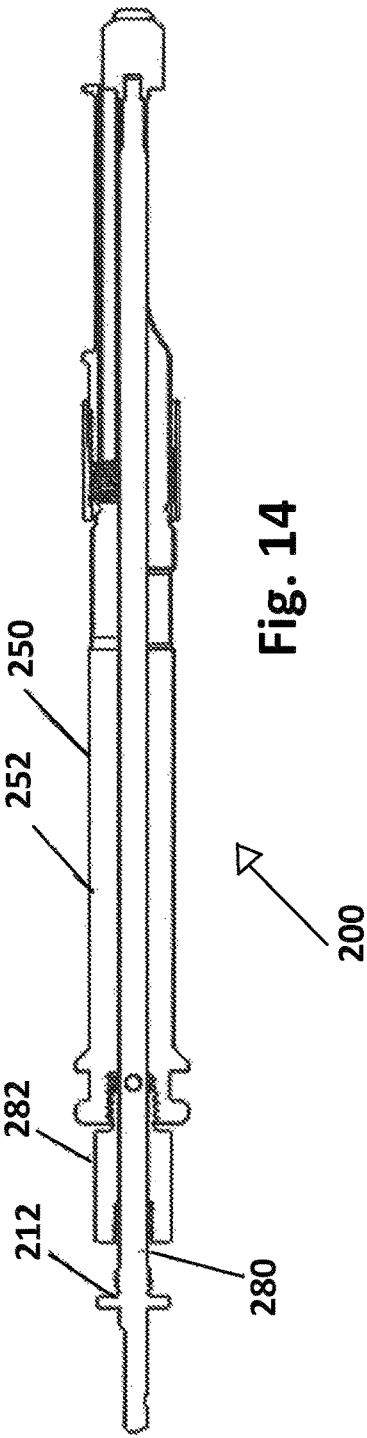
FIG. 14 is a side cross-sectional view of the keel cutter instrument of FIG. 13.

With reference now to FIGS. 13 and 14, there is provided a keel cutter instrument 200 in accordance with another embodiment of the present disclosure. Keel cutter instrument 200 includes an outer assembly 250 and an inner assembly 280. With reference to FIGS. 15 and 16, outer assembly 250 includes a handle 252, an elongate member 254 extending from handle 252, a rotatable sleeve 256, and an outer member 260 including a pusher 257. Outer member 260 is operatively coupled with rotatable sleeve 256 such that rotation of rotatable sleeve 256 causes axial displacement of outer member 260. Elongate member 254 includes a trial sizer 224 configured to be received in the intervertebral space.

With reference now to FIGS. 17-20, inner assembly 280 includes an inner member 283 including keel cutter 262. Inner member 283 is slidably received through elongate member 254 (FIG. 15). In addition, inner assembly 280 further includes a coupling member 282 threadably coupled with handle 252.

Keel cutter 262 is movable relative to inner member 283. Wheel 212 may be selectively engaged with coupling member 282 to define the axial distance such as, e.g., a maximum distance of travel, of keel cutter 262. For example, by increasing the distance between wheel 212 and coupling member 282 through rotation of wheel 212, the distance that can be traveled by keel cutter 262 through rotation of rotatable sleeve 256 may be reduced. As discussed hereinabove, rotation of sleeve 256 causes axial displacement of pusher 257, which, in turn, moves keel cutter 262 up to the amount defined by wheel 212. The method of using keel cutter instrument 200 is substantially identical to the method described hereinabove with respect to keel cutter instrument 10, and thus will not be described herein.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
    an outer assembly defining a longitudinal axis, the outer assembly including a trial sizer configured to be received in an intervertebral space;
    an inner assembly defining a longitudinal axis including an inner member and a keel cutter, the inner member slidably engaged with the inner assembly and operably coupled to a wheel;
    an outer member slidably engaged with the outer assembly; and
    a sleeve coupled with the outer member such that a portion of the outer assembly is received within the sleeve,
    wherein rotation of the sleeve about the longitudinal axis causes the axial displacement of the outer member, and rotation of the wheel about the longitudinal axis causes axial displacement of the inner member.

2. The surgical instrument of claim 1, wherein the outer assembly includes a handle and an elongate member distally extending from the handle, the handle being longitudinally aligned with the elongate member.

3. The surgical instrument of claim 2, wherein the outer member is slidably engaged with the elongate member.

4. The surgical instrument of claim 2, wherein the keel cutter is received within the elongate member, the trial sizer, and the outer member.

5. The surgical instrument of claim 4, wherein the keel cutter is received within a first channel defined by the outer assembly and a second channel defined by the outer member.

6. The surgical instrument of claim 5, wherein the first channel extends from a first end of the elongate member adjacent the handle through a portion of the trial sizer.

7. The surgical instrument of claim 4, wherein the inner member extends from the keel cutter, the inner member being received within a coupling member adjacent a proximal end of the handle.

8. The surgical instrument of claim 7, wherein a first end of the coupling member is configured to threadably engage the proximal end of the handle and a second end of the coupling member is configured to threadably engage a set of threads on the inner member.

9. The surgical instrument of claim 1, wherein the outer member includes a pusher at a distal end of the outer member.

10. The surgical instrument of claim 9, wherein the pusher includes a surface perpendicular to the longitudinal axis and proximal to the trial sizer.

11. A surgical instrument comprising:
    an outer assembly defining a longitudinal axis, the outer assembly including a trial sizer configured to be received in intervertebral space;
    an outer member slidably engaged with the outer assembly, a distal end of the outer member having a pusher proximate to the trial sizer;
    an inner assembly including an inner member and a keel cutter, the keel cutter defining a pair of cutters disposed on opposing portions of the inner member;
    a sleeve coupled with the outer member, wherein rotation of the sleeve about the longitudinal axis affects the axial displacement of the outer member.

12. The surgical instrument of claim 11, wherein the outer assembly comprises a handle and an elongate member distally extending from the handle, the handle being longitudinally aligned with the elongate member.

13. The surgical instrument of claim 12, wherein the outer member is slidably engaged with the elongate member.

14. The surgical instrument of claim 12, wherein the keel cutter is received within the elongate member, the trial sizer, and the outer member.

15. The surgical instrument of claim 14, wherein the keel cutter is received within a first channel defined by the outer assembly and a second channel defined by the outer member.

16. The surgical instrument of claim 15, wherein the first channel extends from a first end of the elongate member adjacent the handle through a portion of the trial sizer.

17. A surgical instrument comprising:
    an outer assembly defining a longitudinal axis, the outer assembly including a trial sizer configured to be received in intervertebral space;

an inner assembly defining a longitudinal axis, the inner assembly including an inner member slidingly engaged with the inner assembly;

an outer member slidably engaged with the outer assembly;

a sleeve coupled with the outer member;

a wheel coupled with the inner member; and a keel cutter received within the outer member and trial sizer, wherein in a first position, the sleeve permits axial displacement of the keel cutter and in a second position, the wheel prevents axial displacement of the keel cutter.

18. The surgical instrument of claim 17, wherein the outer assembly comprises a handle and an elongate member distally extending from the handle, the handle being longitudinally aligned with the elongate member.

19. The surgical instrument of claim 18, wherein the outer member is slidably engaged with the elongate member.

20. The surgical instrument of claim 18, wherein the keel cutter is received within a first channel defined by the outer assembly and a second channel defined by the outer member.

* * * * *